US006689044B2

(12) United States Patent
Kirschabum

(10) Patent No.: US 6,689,044 B2
(45) Date of Patent: Feb. 10, 2004

(54) SUSPENDING BLEEDING WITH A SPECIFIC MAGNET

(76) Inventor: Robert N. Kirschabum, 6630 E. Exposition Ave., Denver, CO (US) 80224

(*) Notice: Subject to any disclaimer, the term of this patent is extended or adjusted under 35 U.S.C. 154(b) by 0 days.

(21) Appl. No.: 09/920,005

(22) Filed: Aug. 1, 2001

(65) Prior Publication Data

US 2002/0045794 A1 Apr. 18, 2002

Related U.S. Application Data

(60) Provisional application No. 60/222,598, filed on Aug. 2, 2000, now abandoned.

(51) Int. Cl.$^7$ .............................. A61B 17/52; A61N 2/00
(52) U.S. Cl. .......................................................... 600/9
(58) Field of Search ........................ 600/9, 15; 128/897, 128/898

(56) References Cited

PUBLICATIONS

"Physical Metallurgy: Structures and properties of metals: magnetic properties", Encyclopedia Britannica, pp. 1–4.*
"Ferromagnetism", Encyclopedia Britannica, pp. 1–3.*
Magnets, Catalog #8, Polar Power Catalog pp. 1, 2, 45, 6, 7, Philpott Medical Services 17171 S. E. 29$^{th}$ Street, Choctaw, OK 73020.
Round Base Magnets, The Magnet Source Catalog, Master Magnetics, Inc., 607 S.Gilbert Castle Rock, CO 80104.

* cited by examiner

Primary Examiner—Max F. Hindenburg
Assistant Examiner—Brian Szmal

(57) ABSTRACT

An arrangement of magnets to be used to deliver a magnetic field deep into the body. The arrangement of magnets causes the alteration of the magnetic field generated by the other magnet to produce an elongated magnetic field that can reach deep into the body. The south pole surfaces of the magnets are attached to one another in a centered arrangement with either adhesives or mechanical fasteners, to focus and project the magnetic field to a greater distance than could be achieved with the magnets individually.

2 Claims, 2 Drawing Sheets

SUSPENDING BLEEDING WITH A SPECIFIC MAGNET

REFERENCE TO RELATED APPLICATIONS

This application claims the benefit of my provisional application having Serial No. 60/222,598, filed Aug. 2, 2000, now abandoned.

BACKGROUND OF THE INVENTION (a) Field of the Invention

This invention generally relates to an arrangement of magnets to be used to deliver a magnetic field deep into the body, and more particularly, but not by way of limitation to a set of magnets that are attached to one another with either adhesives or mechanical fasteners, to focus and project the magnetic field to a greater distance than could be achieved with the magnets individually.

(b) Discussion of Known Art

The use of magnets or magnetic fields to promote healing has gained acceptance due to mounting evidence of their efficacy for this purpose. The evidence has been provided by users who have attributed reduction of symptoms following exposure of maligned areas to magnetic fields. However, an enduring problem associated with the use of magnets, and particularly permanent magnets, for therapeutic purposes has been that the strength of the magnetic fields diminishes to ineffective levels at a short distance below the surface of the body. Thus, there remains a need for a method of providing a magnetic field that can be projected deep into the body from the surface of the skin.

Importantly, there remains a need for a system and method for exposing parts of the body, particularly areas such as bleeding lesions or traumatized areas to magnetic fields that reach deep into the body to effectively expose blood vessels to the magnetic fields to promote healing by exposing the blood flow to the magnetic field.

SUMMARY

It has been discovered that the problems left unanswered by known art can be solved by providing at least two metal clad magnets of different diameters, the magnets arranged so that the larger metallic north pole is placed on the injury site of the body. The magnets will bring about a state of homeostasis. The induced magnetic field will stop bleeding without the formation of a blood scab. I have used the magnets several times and in every instance the magnets are capable of stopping the blood flow from any wound so far encountered. The largest wound was a long gouge caused by a rock, which was three and one-half inches long. The magnets were applied for approximately thirty seconds after which time all bleeding stopped and I was able to walk home (one mile) without any re-bleeding occurring.

The magnets used above are round base magnets with a round nickel plate covering the underlying magnet. According to one example of the invention, the larger magnet has a 2.04 outside diameter, 0.090 inches thick with the magnets inside diameter being 0.865 inches. The smaller magnet has a 1.42 outside diameter, 0.265 inches thick with the magnets inside diameter being 0.375 inches.

The two magnets are attached so that the nickel plates of the two magnets are on the outside. The configuration allows the magnetic North of the larger magnet to be repelled by the smaller magnets magnetic North, causing the magnetic North of the two magnets greater penetration than one would achieve with a single magnet. There is a center hole in each of the magnets. The smaller magnet is placed in the center of the larger magnet with the South Poles of the magnets in direct contact.

If there is an exit wound from the body. The exit wound should also covered.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
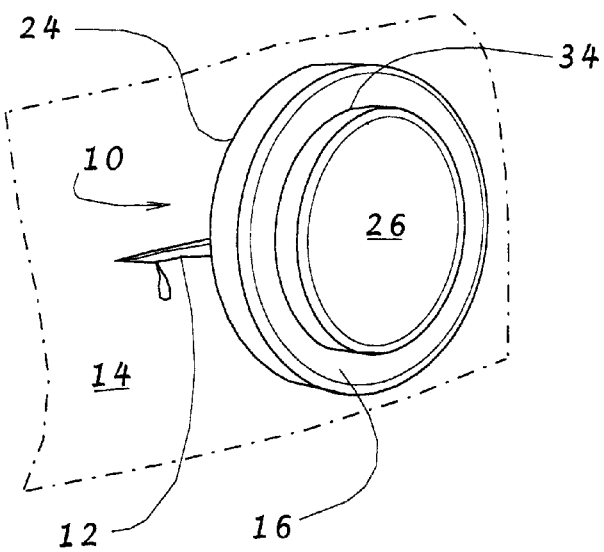
FIG. 1 is a perspective view of an embodiment of the invention.

Turning now to FIG. 1 where an example of the disclosed therapeutic magnet arrangement 10 has been illustrated over a wound 12 in a section of the body 14. The wound 12 may be a newly formed wound that is still bleeding or may be any form of trauma to the body.

Referring to FIGS. 1 through 4 it will be understood that in an important example of the invention the magnet arrangement 10 includes a first magnet 16, the first magnet 16 being generally planar and having a first magnet north surface 18 of a size or area, and a first magnet south surface 20 of a size or area. The first magnet 16 generates a first magnet magnetic field 21. The first magnet 16 also has first magnet perimeter sides 22. In this example, the first magnet north surface 18 and the first magnet perimeter sides 22 are covered by a first magnet plate 24 that is a material that is used to manipulate the magnetic field.

Figure 2:
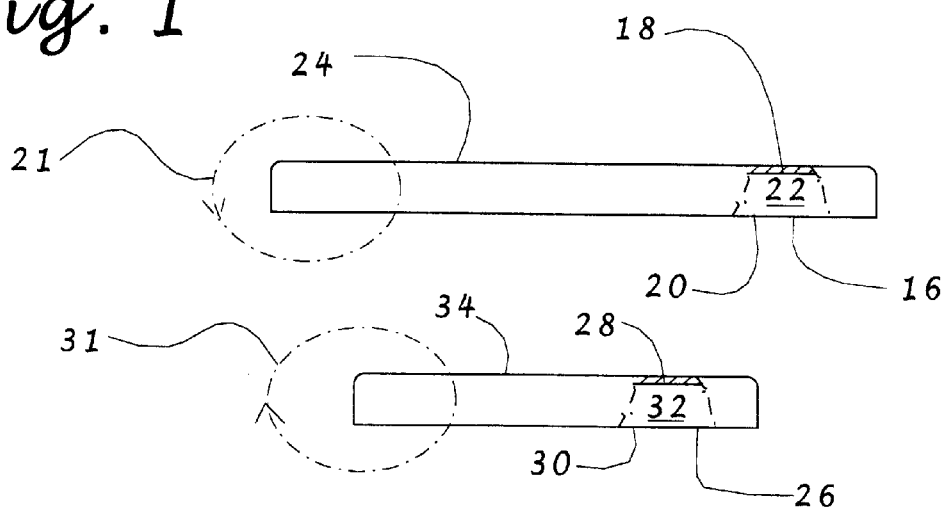
FIG. 2 is an exploded side view of components of the disclosed invention.

Similarly, as illustrated in FIG. 2, a second magnet 26 that is generally planar and includes a second magnet south surface 28 of a size or area, and a second magnet north surface 30 of a size or area. The second magnet 26 generates a second magnet magnetic field 31. The second magnet 26 also has second magnet perimeter sides 32. In this example, the second magnet south surface 28 and the second magnet perimeter sides 32 are covered by a second magnet plate 34 that is of a material that is used to manipulate the magnetic field.

Figure 3:
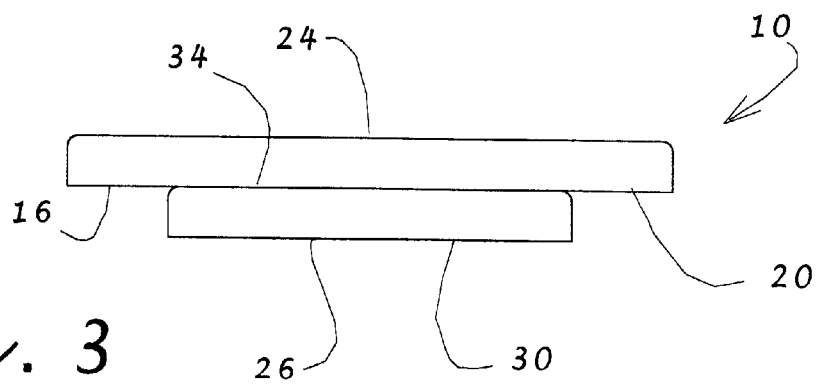
FIG. 3 is a side view of an assembled example of the disclosed invention.

Turning now to FIG. 3 it will be understood that it is contemplated that the first magnet south surface 20 of the first magnet 16 will be attached to the second magnet plate 34 found on the second magnet 26, with the south surface 28 of the second magnet 26 centered over the south surface 20 of the first magnet 16. As illustrated in FIG. 1, it is contemplated that the first magnet 16 and the second magnet 26 will have generally rounded perimeters, making these magnets generally disk or coin shaped. However, it is contemplated that a variety of other shapes may be used.

Figure 4:
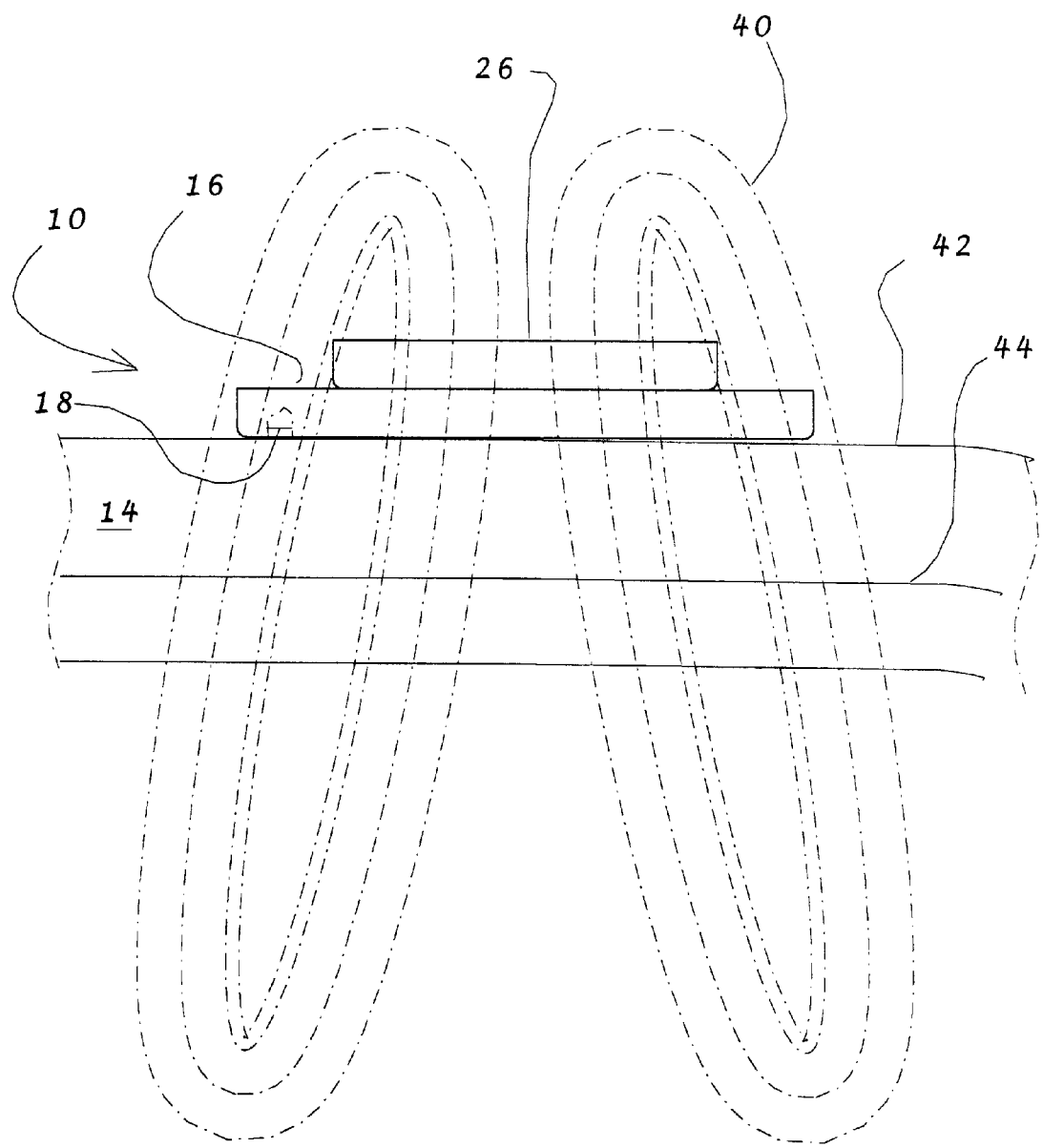
FIG. 4 illustrates an example of the invention in use.

Turning now to FIG. 4, it will be understood that the disclosed arrangement produces focused magnetic fields 40 that, when placed against the skin or surface 42 of the body 14, penetrate deep into the body 14 and reach blood flow paths 44, exposing the blood contained therein to the magnetic fields 40. It has been discovered that the magnetic fields 40 created with the disclosed magnet arrangement assume this dramatically elongated shape that allows the fields to travel deep into the body to achieve the desired therapeutic effects, such as the stopping of bleeding.

EXAMPLE 1

Sinus Relief

An individual from Greeley, Colo., was suffering from pain and congestion stemming from the individual's sinuses. The disclosed magnets were positioned as indicated in FIG. 4 at a location just above the individual's eyes. The individual reported that this helped open his sinuses and eliminated all the pain associated with it.

EXAMPLE 2

Loosen Arthritic Joints

An individual from Aurora, Colo., complained of arthritis was so bad that it did not permit her to straighten her knees without great pain. The severity of her arthritis would come and go, but it had been about two months since the individual could fully bend her knees. Within ten minutes of using the magnets as indicated in FIG. 4, the individual was able to bend her knees and walk without pain. She attributed the pain relief to the use of the invention.

EXAMPLE 3

Insect Bites

A child from Lakewood, Colo., woke-up one morning with a spider bite on his hand. The back of his hand was completely swollen, red and hot. The disclosed invention was placed on his hand as indicated on FIG. 4, and within 30 minutes the redness and swelling was reported to have all but disappeared.

EXAMPLE 4

Reduced Swelling & Pain

A man from Fort Morgan, Colo., reported that about five years prior to using the disclosed invention he had suffered from a broken ankle caused by a car accident. The injury would still bother the individual. The individual reported that use of the invention as illustrated in FIG. 4 was keeping his ankle free of pain. Whenever he felt a tinge in his ankle, he would place the invention over the ankle as shown on FIG. 4 for approximately ten minutes and the pain would be reduced or eliminated.

It is contemplated that the magnets used to carry out the disclosed invention may be of shapes other than the generally disk or rounded shape illustrated in the drawings. It is contemplated that the magnets may be formed from rectangular sections or sections having perimeters of other shapes. It is contemplated that the two magnets may be held together by chemical adhesives or by mechanical fasteners of various materials.

Thus it can be appreciated that the above described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A magnet arrangement for creating a focused magnetic field for placement over an area of the body, the magnet arrangement comprising:

a first magnet that generates a first magnet magnetic field, the first magnet being generally planar and having a first magnet north surface of a first magnet north size, and a first magnet south surface of a first magnet south size, and a first magnet perimeter having sides, the first magnet north surface and the first magnet sides being covered by a plate of a ferrousmagnetic material that is used to manipulate the magnetic field;

a second magnet that generates a second magnetic field, the second magnet being generally planar and including a second magnet having a north surface of a second magnet north size, and a second magnet south surface of a second magnet south size, the second magnet south surface size being smaller than the first magnet south surface size, the second magnet further comprising a second magnet perimeter sides, the second magnet south surface and the second magnet perimeter sides being covered by a second magnet plate that is of a ferrousmagnetic material that is used to manipulate the magnetic field, the second magnet plate being attached to the first magnet south surface, so that the magnetic field generated by the first magnet is altered by the magnetic field generated by the second magnet.

2. A method for exposing a region of the body of an animal to a magnetic field, the method comprising:

providing a magnet arrangement for creating a focused magnetic field for placement over an area of the body, the magnet arrangement comprising:

a first magnet that generates a first magnet magnetic field, the first magnet being generally planar and having a first magnet north surface of a size, a first magnet south surface of a first magnet south surface size, and a first magnet perimeter having sides, the first magnet north surface and the first magnet sides being covered by a first magnet plate that is a material that is used to manipulate the magnetic field;

a second magnet that generates a second magnet magnetic field, the second magnet being generally planar and including a second magnet north surface of a second magnet north surface size, and a second magnet south surface of a second magnet south surface size, the second magnet south surface size being smaller than the first magnet south surface size, the second magnet further comprising a second magnet perimeter sides the second magnet south surface and the second magnet perimeter sides being covered by a second magnet plate that is of a ferrousmagnetic material that is used to manipulate the magnetic field, the second magnet plate being attached to the first magnet south surface, so that the magnetic field generated by the first magnet is altered by the magnetic field generated by the second magnet; and placing the first magnet plate over the area of the body to allow a magnetic field emanating from the magnet arrangement to enter the area of the body.

* * * * *